United States Patent
Owoo et al.

(10) Patent No.: US 8,034,830 B2
(45) Date of Patent: *Oct. 11, 2011

(54) ARGATROBAN FORMULATION

(75) Inventors: George Owoo, North Plainfield, NJ (US); Richard A. Burgos, Rahway, NJ (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/647,854

(22) Filed: Dec. 28, 2009

(65) Prior Publication Data

US 2010/0099706 A1  Apr. 22, 2010

Related U.S. Application Data

(63) Continuation of application No. 11/510,981, filed on Aug. 28, 2006, now Pat. No. 7,642,271.

(60) Provisional application No. 60/713,403, filed on Sep. 1, 2005.

(51) Int. Cl.
*A61K 31/47* (2006.01)
(52) U.S. Cl. ........................................ 514/312
(58) Field of Classification Search ............ 514/312
See application file for complete search history.

(56) References Cited

U.S. PATENT DOCUMENTS

| | | | |
|---|---|---|---|
| 4,227,006 A | 10/1980 | Okamoto et al. | |
| 5,214,052 A | 5/1993 | Ofuchi et al. | |
| 5,506,241 A | 4/1996 | Mano et al. | |
| 5,679,690 A | 10/1997 | Andre et al. | |
| 5,849,843 A | 12/1998 | Laurin et al. | |
| 5,998,019 A | 12/1999 | Rosenbaum et al. | |
| 6,087,375 A | 7/2000 | Bridon et al. | |
| 7,642,271 B2 * | 1/2010 | Owoo et al. | 514/312 |

FOREIGN PATENT DOCUMENTS

| | | |
|---|---|---|
| EP | 0 565 897 | 10/1993 |
| EP | 0 608 828 | 8/1994 |
| EP | 0 608 831 | 8/1994 |
| EP | 0 621 036 | 10/1994 |
| EP | 0 669 131 | 8/1995 |
| WO | 2005/009361 | 2/2005 |

OTHER PUBLICATIONS

Remington—The Science and Practice of Pharmacy 20th Edition, 2000, 9 pages.
GSKARL3-Search performed for acetic acid dissolve argatroban, [online], [retrieved on Aug. 18, 2008], Retrieved from the Internet:<:URL:http://us.gsk.com/products/assets/us_argatroban.pdf>.

* cited by examiner

*Primary Examiner* — Raymond Henley, III
(74) *Attorney, Agent, or Firm* — K&L Gates LLP

(57) ABSTRACT

An aqueous, stable, sterile pharmaceutical composition of the thrombin inhibitor argatroban in a solution containing an acid to solubilize the argatroban, substantially free from dehydrated alcohol is described, as well as a method for its preparation.

17 Claims, 2 Drawing Sheets

ARGATROBAN FORMULATION

CROSS-REFERENCE TO RELATED APPLICATIONS

This application is a continuation of U.S. patent application Ser. No. 11/510,981, now U.S. Pat. No. 7,642,271, filed Aug. 28, 2006, which claims the benefit of U.S. Provisional Patent Application Ser. No. 60/713,403, filed Sep. 1, 2005, the entire contents of which are expressly incorporated herein by reference.

BACKGROUND OF THE INVENTION

The present invention relates to a new pharmaceutical formulation of 1-[5-[(aminoiminomethyl)amino]-1-oxo-2-[[(1,2,3,4-tetrahydro-3-methyl-8-quinolinyl)sulfonyl]amino]pentyl]-4-methyl-2-piperidinecarboxylic acid hydrate, commonly known by the generic name "argatroban." Argatroban is a synthetic direct thrombin inhibitor derived from L-arginine and is a useful anti-coagulant agent.

Argatroban is considered slightly to very slightly soluble in water according to the USP classification of solutes, with solubility on the order of 0.8 to 0.9 mg/mL. It is also both light and heat-sensitive and tends to degrade unless stabilized. Argatroban is commercially available in concentrated form in an aseptically-filled vial containing, per mL, 100 mg argatroban, 750 mg D-sorbitol and 1000 mg dehydrated alcohol. When administered to a patient, this formulation is diluted to a concentration of 1.0 mg/mL in an admixture diluent solution containing an osmotic agent such as sodium chloride or dextrose (c.f. U.S. Pat. No. 5,214,052).

Other formulations of argatroban are described in U.S. Pat. Nos. 5,679,690 and 6,087,375, European Patent Applications 0,565,897 A1 and 0,621,036 A1 and WO 2005/009361 A2.

BRIEF SUMMARY OF THE INVENTION

The present invention provides an aqueous, stable, sterile pharmaceutical composition of a thrombin inhibitor suitable for parenteral administration, substantially free from dehydrated alcohol and having a pH between 3.5 and 8.5 comprising in solution 0.1 to 10 mg/mL 1-[5-[(aminoiminomethyl)amino]-1-oxo-2-[[(1,2,3,4-tetrahydro-3-methyl-8-quinolinyl)sulfonyl]amino]pentyl]-4-methyl-2-piperidinecarboxylic acid hydrate (argatroban) and an acid to solubilize the argatroban. This composition may optionally further contain a buffering agent to help maintain pH and an osmotic-adjusting agent to enhance infusion properties. The composition is storage-stable (both light and heat), capable of being aseptically-filled and heat-sterilized, and contains argatroban in a range of concentrations, from a ready-to-use concentration to a concentrate that requires dilution prior to administration. In a further aspect of the present invention a method is provided for preparing the aforementioned formulation of argatroban in a sealed container, such as an ampoule, vial, syringe or infusion bag, and autoclaving for a period of time sufficient to render the composition sterile.

DETAILED DESCRIPTION OF THE INVENTION

Figure 1:
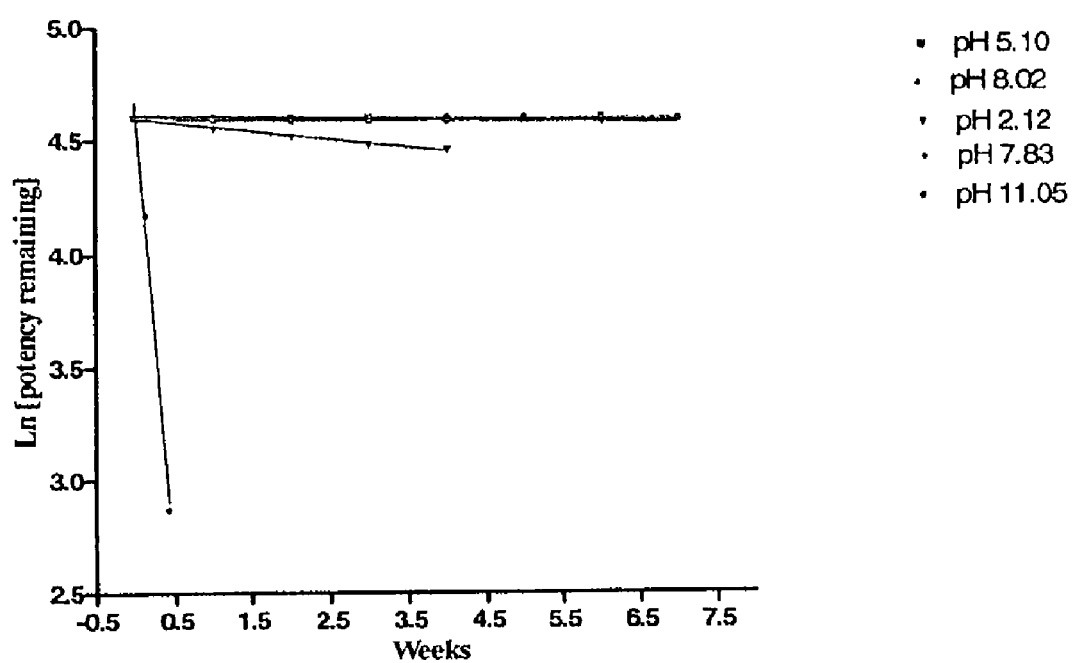
FIG. 1 is a graphical representation of the effect of pH on argatroban content as function of time (weeks) stored at 55° C.

The present invention provides a sterile, stable parenteral composition containing argatroban with enhanced aqueous solubility and optionally a pharmaceutically acceptable buffering agent and an osmotic adjusting agent to adjust the tonicity of the solution. The composition is packaged in a sealed container that may either be aseptically-filled or, preferably, subjected to terminal sterilization to reduce the microbiological burden of the formulation. The present invention is stable against hydrolytic degradation and other adverse chemical reactions, and when packaged appropriately, for example, with an aluminum overpouch, against photolytic degradation.

The enhanced solubility of argatroban in aqueous solution is accomplished by the addition of an acid. The acids will typically be dilute, meaning on the order of 0.01 to 3 N. Though not wishing to be limited to any one theory, it is believed that the acid (which may be either organic or inorganic) forms an "ionic liquid" or in-situ salt solution of argatroban. This refers to an ionic liquid and counter ion of salt where the ions are poorly or randomly arranged and/or coordinated. The ionic liquid/in-situ salt solution may have ions with delocalized charge states, or resonance in the drug molecule that has been stabilized by its counter ion. The effect is that stable solutions of argatroban having solubilities ranging from 0.1 to 10 mg/mL, more commonly 0.8 to 10 mg/mL are possible in spite of being substantially free of solvent or additional solubilizing and/or stabilizing agents, such as ethanol, saccharides, surfactants, long chain fatty acids, cyclodextrin derivatives, caffeine. The solution is thermodynamically stable at room temperature for at least 24 months with essentially no significant degradation and remains within the appropriate pH range.

Table I provides a summary of enhanced solubility of argatroban in dilute acids.

TABLE I

Solubility of Argatroban in dilute acids at room temperature

| Dilute acids[1] | Visual Dissolution[2] | Amount (mg/mL)[3] |
| --- | --- | --- |
| Phosphoric acid | Freely soluble | ≧10.08 |
| Acetic acid | Very soluble | ≧11.5 |
| Tartaric acid | Freely soluble | ≧10.4 |
| Citric acid | Moderately soluble | ≧9.79 |
| Formic acid | Very soluble | ≧10.08 |
| Maleic acid | Moderately soluble | ≧9.32 |
| Hydrochloric acid | Moderately soluble | ≧10.1 |

[1]The molarity of the acids used were ~1-3 N
[2]Classification according to Remington's Pharmaceutical Science, 20$^{th}$ edition
[3]Amount of argatroban was determined by HPLC method "Stable", as used in the context of this application, means remaining in a state or condition that is suitable for administration to a patient. Formulations according to the present invention are found to be stable when maintained at room temperature for at least 24 months, and are generally stable at room temperature for 24 to 36 months.

A "sterile" composition, as used in the context of this application, means a composition that has been brought to a state of sterility and has not been subsequently exposed to microbiological contamination, i.e. the container holding the sterile composition has not been compromised. Sterile compositions are generally prepared by pharmaceutical manufacturers in accordance with current Good Manufacturing Practice ("cGMP") regulations of the U.S. Food and Drug Administration.

The product can take the form of a sterile, stable, ready-to-use formulation for infusion. This avoids the inconvenience of diluting a concentrated argatroban small volume parenteral formulation into infusion diluents prior to infusion, as well as eliminates the risk of microbiological contamination during aseptic handling and any potential calculation or dilution error. Such formulations, not being prepared from a concentrate, will be essentially free from saccharide component, e.g. D-sorbitol, and dehydrated alcohol component, e.g. dehydrated ethanol. The product can also take the form of a concentrated formulation which must be diluted prior to administration.

The aqueous, sterile, stable pharmaceutical composition of the present invention is suitable for parenteral administration to a patient. For example, the composition may be administered in the form of a bolus injection or intravenous infusion. Suitable, routes for parenteral administration include intravenous, subcutaneous, intradermal, intramuscular, intraarticular, and intrathecal. The ready-to-use formulation of the invention is preferably administered by intravenous infusion.

Containers suitable according to the present invention are those known in the art. They include vial, syringe, infusion bag, bottle and ampoule presentations. Containers may be fabricated from glass or from polymeric materials. Ready-to-use formulations are typically packaged in vials, syringes, infusion bags and bottles, while concentrated formulations are typically packaged in ampoules.

The composition of the present invention can be lyophilized by known techniques, and subsequently reconstituted prior to administration. Certain acids in the composition, such as acetic acid, may be volatile and partially lost during lyophilization. In these cases, they must be replenished in the reconstituted solution.

The effect of pH on the degradation of argatroban is studied in five aqueous buffers at 55° C. All buffer solutions are prepared in Water for Injection, in accordance with USP standard buffer solutions. Five buffer solutions are prepared at pH 2.01, 5.0, 7.4, 8.02 and 11.05. For each level, 1 mg/mL of argatroban is accurately weighed and transferred to a calibrated flask. The buffer solution is added to the flask with adequate mixing to dissolve completely, and then diluted to volume. Samples of all five solutions are stored in amber glass (for protection from light) and held at 55° C. Samples are pulled at pre-determined intervals and then analyzed for pH, potency and the physical appearance of the solutions.

The concentration of the drug is determined by a high performance liquid chromatographic (HPLC) method. The data obtained is plotted as a log of drug concentration versus time with the assumption that the rate reaction is apparent first-order ($k_{observed}$). Degradation rate of the argatroban at accelerated temperature of 55° C. versus various pH values is monitored and a pictorial representation is shown in FIG. 1. The $k_{observed}$ is calculated from the slopes of the linear regression lines, and maximum changes in the degradation rate are both at low and high pH values of (pH 2.0 and 11.05). The lowest $k_{observed}$ in this study is seen in the range from pH 5.0 to about pH 8.0, suggesting that the pH of the composition should be controlled for maximum stability. The results indicate that the pH should be between 3.5 and 8.5, preferably between 4.5 and 6.5, more preferably about 4.5 to 5.5. The pH can be adjusted as known in the art by addition of sodium hydroxide or acetic acid.

Figure 2:
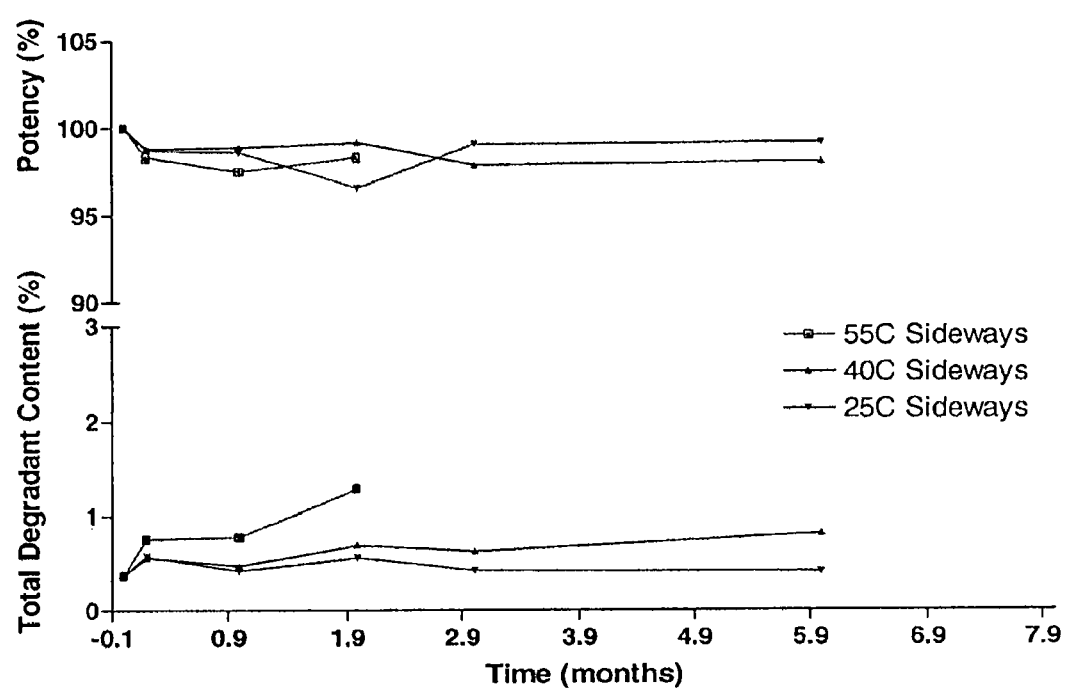
FIG. 2 is a graphical representation of solution stability for 1 mg/mL argatroban injection under various temperature conditions as a function of time.

The ready-to use formulation of argatroban injection is subjected to stress studies to predict the shelf life of the product in aqueous media. Solutions of argatroban composition after autoclave cycle of 121° C. for 20 minutes with minimal degradation are stored at 25° C., 40° C. and 55° C. (protected from light) for a six-month period. The pH, potency, particulate matter and the physical appearance of the solutions are determined. The concentration of the drug is determined by a high performance liquid chromatographic (HPLC) method. Data obtained from this study indicate that the stabilization effect is maximized at pH 5.0±0.5 and the total degradants change over the period studied at 40° C. is less than 1%. Regression and extrapolation of the stability data obtained suggests a shelf life of aqueous composition of not less than 24 months at room temperature (25° C.). FIG. 2 is a plot of solution stability for 1 mg/mL argatroban injection under various temperature conditions as a function of time.

Moreover, it has been determined that no buffering agent is necessary when the argatroban composition of the present invention is stored in certain types of containers since the argatroban composition is inherently stable. Suitable such containers are those whose surfaces in contact with the argatroban composition do not contain leachable substances, which are typically alkaline. One such suitable container is Baxter Healthcare Corporation's IntraVia® flexible plastic container. The pHs of the compositions in the case where no buffering agent is used will generally range from about 4.5 to 5.5.

Argatroban is present in the present composition in an amount ranging from 0.1 to 10 mg/mL. Ready-to-use formulations may contain 0.5 to 10 mg/mL, more commonly about 1 mg/mL argatroban.

Acids used to solubilize the argatroban may be organic or inorganic. Suitable such acids include phosphoric acid, acetic acid, tartaric acid, citric acid, formic acid, malic acid, hydrochloric acid and mixtures thereof. They are typically employed in the solution at concentrations ranging from 0.01 to 3 N, depending on the degree of ionization and association of the counter-ion stability in an aqueous environment. The preferred acid is acetic acid, and will be present in an amount ranging from 0.5 to 6 mg/mL.

Suitable physiologically-acceptable buffering agents include acetate, glutamate, citrate, tartrate, benzoate, lactate, malate, gluconate, phosphate and glycine, with acetate being preferred. The preferred buffering system comprises a combination of sodium acetate and acetic acid. Buffering agents are present in the composition in a concentration that depends from the concentration of argatroban. The concentration will typically range from 0.05 to 200 mM, and from 10 to 100 mM for formulations containing 0.5 to 10 mg/mL argatroban.

Suitable osmotic-adjusting agents, when used, are compatible with the pH requirements of the present formulation, and include one or more of sodium chloride, calcium chloride, potassium chloride, dextrose and sodium lactate. Preferred are sodium chloride and dextrose. The formulations of the present invention may contain 1 to 100 mg/mL osmotic-adjusting agent; preferably 4 to 60 mg/mL sodium chloride, more preferably 4 to 10 mg/mL sodium chloride; or dextrose at a level no greater than 5% (weight by weight), typically in an amount ranging from 25 to 60 mg/mL.

Compositions according to the present invention can be prepared into small volume parenteral (SVP) and large volume parenteral (LVP) dosage forms. The dosage forms can be held in any suitable container. Suitable containers include, for example, glass or polymeric vials, ampoules, syringes or infusion bags with sizes ranging from 1 ml to 500 ml. SVP ready-to-use solutions are typically filled into ampules and vials in 1 to 100 mL presentations. In addition, syringes can be used as the container for a ready-to-use SVP, which are sold as "pre-filled syringes". The LVP presentations can be contained in infusion bags or bottles.

Polymeric containers are preferably flexible and can contain or be free of polyvinylchloride (PVC). Preferred containers are free of PVC, such as those disclosed in U.S. Pat. Nos. 5,849,843 and 5,998,019. Polymeric containers can further be provided with a moisture barrier as a secondary packaging system to prevent the loss of water during storage and to further ensure the stability of the formulation. A preferred moisture barrier is an aluminum overpouch, which will also protect the formulation from photolytic degradation.

Procedures for filling compositions of the present invention in containers, and their subsequent processing are known in the art. These procedures are used to produce sterile pharmaceutical drug products often required for health care. Such processing techniques preferably use a sterilization process to destroy or eliminate any microorganisms that may be present in the argatroban formulations following preparation. For example, terminal heat sterilization can be used to destroy all viable microorganisms within the final, sealed container of the argatroban formulation. An autoclave is commonly used to accomplish terminal heat-sterilization of drug products in their final packaging.

Typical autoclave cycles in the pharmaceutical industry to achieve terminal sterilization of the final product are 121° C. for 15 minutes. The argatroban composition of the present invention can be autoclaved at a temperature ranging from 115 to 130° C. for a period of time ranging from 5 to 40 minutes with acceptable stability. Autoclaving is preferably carried out in the temperature range of 119 to 122° C. for a period of time ranging from 10 to 36 minutes.

Alternatively, sterile pharmaceutical compositions according to the present invention may be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization, prior to filling. The container (e.g., vial, ampoule, infusion bag, bottle, or syringe) are then filled under aseptic conditions.

The following examples further illustrate the invention but should not be construed as in any way limiting its scope. In each case, a 1 mg/mL formulation is prepared.

Example 1

| | |
|---|---|
| Argatroban | 1 mg |
| Acetic Acid, USP | 0.546 mg |
| Sodium Acetate Trihydrate, USP | 2.8 mg |
| NaCL, USP osmotic adjusting agent | 5.9 mg |
| Acetic acid or NaOH | To adjust pH as required |
| Water for Injection, USP | q.s. |
| Autoclave cycle = 121° C., for 2 to 20 minutes | |

Example 2

| | |
|---|---|
| Argatroban | 5 mg |
| Acetic Acid, USP | 0.546 mg |
| NaCL, USP osmotic adjusting agent | 5.9 mg |
| Acetic acid or NaOH | To adjust pH as required |
| Water for Injection, USP | q.s. |
| Autoclave cycle = 121° C., for 2 to 20 minutes | |

Example 3

| | |
|---|---|
| Argatroban | 1 mg |
| Phosphoric Acid, USP | 8.5 mg |
| Sodium Phosphate | 1.8 mg |
| NaCL, USP osmotic adjusting agent | 5.9 mg |
| Acetic acid or NaOH | To adjust pH as required |
| Water for Injection, USP | q.s. |
| Autoclave cycle = 121° C., for 2 to 20 minutes | |

Example 4

| | |
|---|---|
| Argatroban | 10 mg |
| Hydrochloric acid | 0.146 mg |
| NaCl, USP osmotic adjusting agent | 5.9 mg |
| HCl or NaOH | To adjust pH as required |
| Water for Injection, USP | q.s. |
| Autoclave cycle = 121° C., for 2 to 20 minutes | |

Example 5

| | |
|---|---|
| Argatroban | 1 mg |
| Tartaric Acid, USP | 12.3 mg |
| NaCl, USP osmotic adjusting agent | 5.9 mg |
| Tartaric acid or NaOH | To adjust pH as required |
| Water for Injection, USP | q.s. |
| Autoclave cycle = 121° C., for 2 to 20 minutes | |

Example 6

| | |
|---|---|
| Argatroban | 5 mg |
| Critic Acid, USP | 15 mg |
| Sodium Citrate | 1.2 mg |
| NaCl, USP osmotic adjusting agent | 5.9 mg |
| Critic Acid, or NaOH | To adjust pH as required |
| Water for Injection, USP | q.s. |
| Autoclave cycle = 121° C., for 2 to 20 minutes | |

Example 7

| | |
|---|---|
| Argatroban | 1 mg |
| Acetic Acid, USP | 0.546 mg |
| Sodium Acetate Trihydrate, USP | 2.8 mg |
| Dextrose, USP osmotic adjusting agent | 50 mg |
| Acetic acid or NaOH | To adjust pH as required |
| Water for Injection, USP | q.s. |
| Autoclave cycle = 121° C., for 2 to 20 minutes | |

Example 8

| | |
|---|---|
| Argatroban | 5 mg |
| Acetic Acid, USP | 0.546 mg |
| Sodium Acetate Trihydrate, USP | 2.8 mg |
| (No osmotic adjusting agent) | |
| Acetic acid or NaOH | To adjust pH as required |
| Water for Injection, USP | q.s. |
| Autoclave cycle = 121° C., for 2 to 20 minutes | |

Example 9

| | |
|---|---|
| Argatroban | 5 mg |
| Formic Acid, USP | 3.6 mg |
| NaCl, USP osmotic adjusting agent | 5.9 mg |
| Formic acid or NaOH | To adjust pH as required |
| Water for Injection, USP | q.s. |
| Autoclave cycle = 121° C., for 2 to 20 minutes | |

Procedure

The equipment and glassware for compounding, filtering, and filling are properly washed and depyrogenated. The filter assembly, filling tube assembly, and other parts and equipment are sterilized.

Eighty percent (80%) of the final volume of cool Water for Injection is collected in a calibrated compounding tank. Sodium chloride is added to the tank and the solution is stirred until sodium chloride is dissolved. Sodium acetate is then added to the tank, stirred until all excipients are dissolved. The tank is adjusted to 90% of final volume with Water for Injection and mixed. Approximately 1.08 grams of acetic acid is added 2 liter of water to prepare of a slurry solution of argatroban. Argatroban is weighed into the 2 liter acidified water to form a slurry solution. This slurry is then added to the compounding tank and the solution is mixed. The solution is then adjusted to pH 5.5 with 1 N sodium hydroxide or acetic acid if necessary. The solution is brought to final volume with Water for Injection and mixed.

The solution is then filled into 250 ml non-PVC flexible bags (IntraVia® flexible plastic container (PL 2408-3 non-PVC multi-layer plastic film) with one standard PL 146.RTM. PVC membrane tube, one PL 2409-3 multi-layer plastic co-extruded administration port tube, one PL 141 PVC blue-tip closure (administration port protector), available from Baxter Healthcare Corporation). These bags are sealed in aluminum foil overpouches. The products are then loaded into an autoclaving sterilizer and sterilized at 121° C. for 20 minutes.

What is claimed is:

1. An aqueous, stable, injectable, sterile pharmaceutical solution comprising:
    a) 0.5 to 10 mg/mL 1-[5-[(aminoiminomethyl)amino]-1-oxo-2-[[(1,2,3,4-tetrahydro-3-methyl-8-q-uinolinyl)sulfonyl]amino]pentyl]-4-methyl-2-piperidinecarboxylic acid hydrate (argatroban);
    b) 0.01 to 3 N acid to solubilize the argatroban;
    c) a buffering agent to maintain the solution at a pH of about 4.5 to 5.5; and
    d) 1 to 100 mg/ml osmotic-adjusting agent, wherein the pharmaceutical solution is stable for at least 24 months and is free from dehydrated alcohol.

2. The pharmaceutical solution of claim 1, wherein the buffering agent comprises at least one of acetate, glutamate, citrate, tartrate, benzoate, lactate, malate, gluconate, phosphate and glycine.

3. The pharmaceutical solution of claim 1, wherein the osmotic-adjusting agent comprises at least one of sodium chloride, calcium chloride, potassium chloride, dextrose and sodium lactate.

4. The pharmaceutical solution of claim 1, wherein the acid comprises at least one of phosphoric acid, acetic acid, tartaric acid, citric acid, formic acid, malic acid and hydrochloric acid.

5. The pharmaceutical solution of claim 1, wherein the solution is provided in a heat-sterilized container.

6. The pharmaceutical solution of claim 5, wherein the heat-sterilized container is a vial, ampoule, syringe, infusion bag or bottle.

7. The pharmaceutical solution of claim 1 comprising per 1 mL:
    a) 1 to 10 mg 1-[5-[(aminoiminomethyl)amino]-1-oxo-2-[[(1,2,3,4-tetrahydro-3-methyl-8-quinolinyl)sulfonyl]amino]pentyl]-4-methyl-2-piperidinecarboxylic acid hydrate (argatroban);
    b) 0.5 to 6 mg acetic acid to solubilize the argatroban; and
    c) 1 to 100 mg NaCl osmotic-adjusting agent.

8. The pharmaceutical solution of claim 1, wherein the pharmaceutical solution is stable at room temperature for 24 to 36 months.

9. A ready-to-use argatroban product comprising:
    a heat-sterilized container comprising a stable, injectable, sterile pharmaceutical solution comprising:
    a) 0.5 to 10 mg/mL 1-[5-[(aminoiminomethyl)amino]-1-oxo-2-[[(1,2,3,4-tetrahydro-3-methyl-8-q-uinolinyl)sulfonyl]amino]pentyl]-4-methyl-2-piperidinecarboxylic acid hydrate (argatroban);
    b) 0.01 to 3 N acid to solubilize the argatroban;
    c) a buffering agent to maintain the solution at a pH of about 3.5 to 8.5; and
    d) 1 to 100 mg/ml osmotic-adjusting agent, wherein the pharmaceutical solution is free from dehydrated alcohol.

10. The ready-to-use argatroban product of claim 9, wherein the buffering agent comprises at least one of acetate, glutamate, citrate, tartrate, benzoate, lactate, malate, gluconate, phosphate and glycine.

11. The ready-to-use argatroban product of claim 9, wherein the osmotic-adjusting agent comprises at least one of sodium chloride, calcium chloride, potassium chloride, dextrose and sodium lactate.

12. The ready-to-use argatroban product of claim 9, wherein the acid comprises at least one of phosphoric acid, acetic acid, tartaric acid, citric acid, formic acid, malic acid and hydrochloric acid.

13. The ready-to-use argatroban product of claim 9 comprising per 1 mL:
    a) 1 to 10 mg 1-[5-[(aminoiminomethyl)amino]-1-oxo-2-[[(1,2,3,4-tetrahydro-3-methyl-8-quinolinyl)sulfonyl]amino]pentyl]-4-methyl-2-piperidinecarboxylic acid hydrate (argatroban);
    b) 0.5 to 6 mg acetic acid to solubilize the argatroban; and
    c) 1 to 100 mg NaCl osmotic-adjusting agent.

14. The ready-to-use argatroban product of claim 9, wherein the pharmaceutical solution is stable at room temperature for 24 to 36 months.

15. The ready-to-use argatroban product of claim 9, wherein the heat-sterilized container is a vial, ampoule, syringe, infusion bag or bottle.

16. The ready-to-use argatroban product of claim 9, wherein the heat-sterilized container is a polymeric bag free from polyvinyl chloride.

17. A ready-to-use argatroban product comprising:

a heat-sterilized polymeric bag comprising an aluminum overpouch, the polymeric bag containing a stable, injectable, sterile pharmaceutical solution comprising:

a) 0.5 to 10 mg/mL 1-[5-[(aminoiminomethyl)amino]-1-oxo-2-[[(1,2,3,4-tetrahydro-3-methyl-8-q-uinolinyl)sulfonyl]amino]pentyl]-4-methyl-2-piperidinecarboxylic acid hydrate (argatroban);

b) 0.01 to 3 N acid to solubilize the argatroban;

c) a buffering agent to maintain the solution at a pH of about 3.5 to 8.5; and d) 1 to 100 mg/ml osmotic-adjusting agent, wherein the pharmaceutical solution is free from dehydrated alcohol.

* * * * *